United States Patent [19]

Jain et al.

[11] 4,330,296

[45] May 18, 1982

[54] ALBUMIN REAGENT AND ASSAY

[75] Inventors: Chandra P. Jain, Placentia; Frank R. Shu, Anaheim, both of Calif.

[73] Assignee: Beckman Instruments, Inc., Fullerton, Calif.

[21] Appl. No.: 161,833

[22] Filed: Jun. 23, 1980

[51] Int. Cl.$^3$ ...................... G01N 21/29; G01N 33/68
[52] U.S. Cl. .................................. 23/230 B; 23/902; 252/408
[58] Field of Search ...................... 23/230 B, 902, 909; 252/408

[56] References Cited

U.S. PATENT DOCUMENTS

| | | | |
|---|---|---|---|
| 3,533,749 | 10/1970 | Kleinman | 23/230 B |
| 3,873,272 | 3/1975 | Wakefield et al. | 23/230 B |
| 3,884,637 | 5/1975 | Gindler | 23/230 B |

OTHER PUBLICATIONS

Doumas et al., *Clin. Chim. Acta,* 31:87–96 (1971).
Gustafsson, *Clin. Chim.* 22 (5):616–622 (1976).

*Primary Examiner*—Arnold Turk
*Attorney, Agent, or Firm*—R. J. Steinmeyer; J. E. Vanderburgh; Robert S. Frieman

[57] ABSTRACT

An albumin reagent of the type comprising bromcresol green, a buffering agent having a buffering capacity in the pH range of about 4 to about 4.2, and polyoxyethylene(23) lauryl ether. The albumin reagent is characterized in that it contains from about 0.18 to about 0.22 gm/l bromcresol green and has a polyoxyethylene(23) lauryl ether:bromcresol green weight ratio of from about 10:1 to about 12:1.

6 Claims, No Drawings

ALBUMIN REAGENT AND ASSAY

BACKGROUND OF THE INVENTION

1. Field of the Invention

This invention pertains to a reagent for use in measuring albumin and, in particular, to an albumin reagent of the type comprising bromcresol green (also known as bromocresol green) and polyoxyethylene(23) lauryl ether.

2. Description of the Prior Art

The use of a reagent comprising, inter alia, bromcresol green (BCG) and polyoxyethylene(23) lauryl ether (manufactured by ICI Americas, Inc., Wilmington, Del. 19897 under the trademark BRIJ-35) has been reported by various investigators (1–3). Doumas et al. (1) report that the use of the nonionic surfactant polyoxyethylene(23) lauryl ether reduces the absorbance of the blank, prevents turbidity, and improves linearity. Doumas et al. (1) state that concentrations of polyoxyethylene(23) lauryl either greater than or less than 1.2 grams per liter (gm/l) result in decreased sensitivity and loss of linearity.

SUMMARY OF THE INVENTION

This invention encompasses an albumin reagent of the type comprising BCG, a buffering agent having a buffering capacity in the pH range of about 4 to about 4.2, and polyoxyethylene(23) lauryl ether. The reagent is characterized in that it contains from about 0.18 to about 0.22 gm/l BCG and has a polyoxyethylene(23) lauryl ether:BCG weight ratio of from about 10 to about 12. The reagent of the instant invention has a linearity superior to the reagent of Doumas et al. (1).

Still other features and attendant advantages of the present invention will become apparent to those skilled in the art from a reading of the following detailed description of the preferred embodiments.

DESCRIPTION OF THE PREFERRED EMBODIMENTS

The albumin reagent of the instant invention is of the type comprising BCG, a buffering agent, and polyoxyethylene(23) lauryl ether. Any buffering agent having a buffering capacity in the pH range of from about 4 to about 4.2 can be employed in this invention. Examples of such buffering agents include, but are not limited to, a combination comprising an alkali metal hydroxide and a substance selected from a group consisting of succinic acid and citric acid. Preferably, the buffering agent comprises sodium hydroxide and succinic acid in amounts capable of yielding the desired pH.

The albumin reagent of the instant invention can further comprise a preservative agent. Virtually any preservative agent which does not interfere with the albumin assay to be performed can be employed in this invention. Examples of such preservative agents include, but are not limited to, sodium azide, 2-bromo-2-nitro-1,3-propanediol, and dimethoxane. The preferred preservative for use in the instant invention is 2-bromo-2-nitro-1,3-propanediol.

The reagent of the instant invention can be employed in any of the known dye-binding methods for measuring albumin wherein the dye employed therein is BCG. Typically, the methodology can employ the steps of contacting the sample to be assayed with the BCG containing reagent and measuring the absorbance of the resulting solution. The absorbance can be measured at either from about 600 to about 630 nm or about 426 nm.

The sample to be assayed can be either serum or cerebral spinal fluid.

The following examples are provided for the purpose of further illustration only and are not to be limitations on the disclosed invention.

EXAMPLE 1

The following is the composition of the preferred reagent of the instant invention:

| Ingredients | Concentration, gm/l |
|---|---|
| Buffer | |
| Sodium hydroxide | 1.6 |
| Succinic Acid | 8.9 |
| 2-bromo-2-nitro-1,3-propanediol | 0.05 |
| BCG | 0.2 |
| Polyoxyethylene(23) lauryl ether | 2 |

EXAMPLE 2

Albumin standards (2.0, 4.0, and 6.0 grams per deciliter (gm/dl)) were assayed with a reagent within the scope of the instant invention, i.e., the reagent of Example 1, on a colorimeter using the following parameters:

| | |
|---|---|
| Sample size | 5 μl |
| Reagent volume | 1 ml |
| Wavelength | 630 nm |
| Reaction time | 10 sec. |
| Optical path | 1 cm |
| Reaction temperature | ambient |

The data, in terms of absorbance, obtained from this experiment is set forth in Table I.

EXAMPLE 3

The albumin standards employed in Example 2 were assayed with the prior art ragent of Doumas et al. (1) in conjunction with the colorimeter and parameters described in Example 2. The data, in terms of absorbance, obtained from this experiment is also set forth in Table I.

TABLE I

| | Reagent Within Scope of this Invention | | Prior Art Reagent of Doumas et al. (1) | |
|---|---|---|---|---|
| Standard gm/dl | Absorbancy xg[1] | Recovery, gm/dl | Absorbance xg | Recovery, gm/dl |
| 2.0 | 75.0 | 2.0 | 82.9 | 1.8 |
| 4.0 | 150.2 | 4.0 | 159.3 | 4.3 |
| 6.0 | 231.8 | 6.1 | 220.0 | 6.3 |
| 8.0 | 298.6 | 7.9 | 263.7 | 7.7 |

[1]Absorbance xg denotes absorbance times gain, the gain being a constant.

In order to properly compare the linearity of the data obtained with the Doumas et al. reagent (1) to the linearity of the data obtained with a reagent within the scope of this invention, it is first necessary to determine the equations for the straight lines which best fit through each reagent's respective set of data points. This was readily accomplished via the well known linear regression analysis method. After having obtained the line of best fit for each set of data points, each line was employed in conjunction with its respective set of absorbance data to determine the amount of albumin recovered for each of the reagents tested. This recovery data is also set forth in Table I.

A visual comparison of the two sets of recovery data indicates that the reagent within the scope of the present invention possesses a better linearity than the prior art reagent of Doumas et al. (1) in that the recovery data for this invention's reagent approximates a true mathematical progression better than the recovery data obtained via the prior art Doumas et al. (1) reagent.

EXAMPLE 4

The albumin standards set forth in Table II were assayed with a reagent within the scope of this invention, i.e., the reagent of Example 1, on the colorimeter channel of an Astra TM multichannel analyzer sold by Beckman Instruments, Inc., Fullerton, Calif. 92634. The following parameters were used in the performance of each assay:

| | |
|---|---|
| Sample size | 7 μl |
| Reagent volume | 1 ml |
| Wavelength | 600 nm |
| Reaction | 10 sec. |
| Optical path | 1 cm |
| Reaction temperature | ambient |

The colorimeter channel was calibrated with (1) a standard containing 5.00 mg/dl human serum albumin (HSA) and (2) a saline solution devoid of albumin. The data obtained from this experiment is set forth in Table II.

EXAMPLE 5

The albumin standards set forth in Table II were assayed with a commercial reagent comprising 2.00 gm/l sodium hydroxide, 0.12 gm/l BCG, 9.74 gm/l succinic acid, 1.5 gm/l polyoxyethylene(23) lauryl ether, and an undisclosed amount of an undisclosed preservative. The assays were performed in conjunction with the colorimeter channel of the Astra TM multichannel analyzer and parameters described in Example 4. The colorimeter channel was calibrated with (1) the standard and (2) saline solutes employed in Example 4. The data obtained from this experiment is also set forth in Table II.

TABLE II

| Sample | Composition of Sample | Assigned Value, gm/dl | Reagent Within Scope of This Invention, gm/dl | Prior Art Commercial Reagent, gm/dl |
|---|---|---|---|---|
| Calibrator 1 | HSA/γ-G$^i$ | 5.00$^c$ | 5.00 | 5.00 |
| Calibrator 2 | Aqueous | 0.00$^d$ | 0.00 | 0.00 |
| 1 | HSA$^a$ | 4.0$^e$ | 4.10 | 4.22 |
| 2 | BSA$^b$ | 7.0$^f$ | 6.97 | 6.31 |
| 3 | BSA | 2.0$^g$ | 1.95 | 1.99 |
| 4 | BSA | 4.0$^g$ | 4.14 | 3.94 |
| 5 | BSA | 6.0$^g$ | 6.24 | 5.53 |
| 6 | BSA | 8.0$^g$ | 8.13 | 6.86 |
| 7 | BSA | 10.0$^g$ | 9.91 | 8.00 |
| 8 | HSA | 2.0$^h$ | 1.84 | 1.99 |
| 9 | HSA | 4.0$^h$ | 3.98 | 4.08 |
| 10 | HSA | 6.0$^h$ | 6.06 | 5.98 |
| 11 | HSA | 8.0$^h$ | 7.96 | 7.68 |
| 12 | HSA | 10.0$^h$ | 9.88 | 9.21 |

$^a$HSA denotes human serum albumin.
$^b$BSA denotes bovine serum albumin.
$^c$Human protein standard sold by Sigma Chemical Company.
$^d$Saline solution devoid of albumin.
$^e$Total protein standard sold by Dade Division of American Hospital Supply.
$^f$National Bureau of Standards' total protein reference material.
$^g$Albumin standard sold by New England Reagent Laboratory.
$^h$Standards made by diluting a 10% HSA standard sold by Miles Laboratories.
$^i$HSA/γ-G denotes a mixture containing HSA and γ-globulin fractions.

As shown in Table II, when compared to the data obtained via the same albumin assay employing a prior art albumin reagent, an albumin assay performed with a reagent within the scope of this invention (i.e., with an albumin reagent characterized in that it contains from about 0.18 to about 0.22 gm/l BCG and has a polyoxyethylene(23) lauryl ether:BCG weight ration of from about 10 to about 12) yields data which tends to deviate less from the assayed sample's assigned value.

Based on this disclosure, many other modifications and ramifications will naturally suggest themselves to those skilled in the art. These are intended to be comprehended as within the scope of this invention.

REFERENCES

1. Doumas et al., Clin. Chim. Acta, 31:87–96 (1971).
2. Gustafsson, Clin. Chim. 22(5):616–622 (1976).
3. U.S. Pat. No. 3,884,637.

The embodiments of the invention in which an exclusive property or privilege is claimed are defined as follows:

1. An albumin reagent of the type comprising bromcresol green, a buffering agent having a buffering capacity in the pH range of about 4 to about 4.2, and polyoxyethylene(23) lauryl ether, characterized in that the reagent contains from about 0.18 to about 0.22 gm/l bromcresol green and has a polyoxyethylene(23) lauryl ether:bromcresol green weight ratio of from about 10:1 to about 12:1.

2. The albumin reagent of claim 1 further comprising a preservative agent.

3. The albumin reagent of claim 1 wherein said buffering agent comprises an alkali metal hydroxide and a substance selected from a group consisting of succinic acid and citric acid.

4. The albumin reagent of claim 3 further comprising a preservative agent selected from a group consisting of sodium azide, 2-bromo-2-nitro-1,3-propanediol, and dimethoxane.

5. The albumin reagent of claim 1 comprising about 0.2 gm/l of bromcresol green, about 8.9 gm/l of succinic acid, about 1.6 gm/l of sodium hydroxide, about 2 gm/l of polyoxyethylene(23) lauryl ether, and about 0.05 gm/l of 2-bromo-2-nitro-1,3-propanediol.

6. An albumin assay of the type comprising:
(a) contacting a sample to be assayed with an albumin reagent; and
(b) measuring the absorbance of the resulting solution, characterized in that the albumin reagent employed therein is the reagent of any one of claims 1–4 or 5.

* * * * *

Disclaimer 4,330,296.—*Chandra P. Jain*, Placentia, and *Frank R. Shu*, Anaheim, Calif. ALBUMIN REAGENT AND ASSAY. Patent dated May 18, 1982. Disclaimer filed Aug. 21, 1986, by the assignee, *Beckman Instruments, Inc.*

The term of this patent subsequent to June 26, 1986, has been disclaimed.
[*Official Gazette October 21, 1986.*]

REEXAMINATION CERTIFICATE (703rd)
United States Patent [19]
Jain et al.

[11] B1 4,330,296
[45] Certificate Issued Jun. 9, 1987

[54] ALBUMIN REAGENT AND ASSAY

[75] Inventors: Chandra P. Jain, Placentia; Frank R. Shu, Anaheim, both of Calif.

[73] Assignee: Beckman Instruments, Inc., Fullerton, Calif.

Reexamination Reqs:st:
No. 90/000,665, Nov. 9, 1984
No. 90/000,835, Aug. 13, 1985

Reexamination Certificate for:
Patent No.: 4,330,296
Issued: May 18, 1982
Appl. No.: 161,833
Filed: Jun. 23, 1980

[51] Int. Cl.[4] ................... G01N 21/29; G01N 33/68
[52] U.S. Cl. .................................................... 436/88
[58] Field of Search ................................. 436/86–88

[56] References Cited

U.S. PATENT DOCUMENTS

3,533,749 10/1970 Kleinman .
3,873,272 3/1975 Wakefield et al. .
3,884,637 5/1975 Gindler .

OTHER PUBLICATIONS

Doumas et al., Clin. Chim. Acta, 31:87–96 (1971).
Gustafsson, Clin. Chim., 22 (5):616–622 (1976).
Corcoran et al., Clinical Chemistry, vol. 23, No. 4, (1977), pp. 765–766.
Doumas et al., "Standard Methods in Clinical Chemistry", vol. 7, Academie Press, 1972, pp. 175–188.

*Primary Examiner*—Michael S. Marcus

[57] ABSTRACT

An albumin reagent of the type comprising bromcresol green, a buffering agent having a buffering capacity in the pH range of about 4 to about 4.2, and polyoxyethylene(23) lauryl ether. The albumin reagent is characterized in that it contains from about 0.18 to about 0.22 gm/l bromcresol green and has a polyoxyethylene(23) lauryl ether:bromcresol green weight ratio of from about 10:1 to about 12:1.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-6 are cancelled.

* * * * *